US007890348B2

(12) United States Patent
Aluri et al.

(10) Patent No.: US 7,890,348 B2
(45) Date of Patent: Feb. 15, 2011

(54) TEXT-BASED GENERIC SCRIPT PROCESSING FOR DYNAMIC CONFIGURATION OF DISTRIBUTED SYSTEMS

(75) Inventors: Srinivas Aluri, Pewaukee, WI (US);
Medhi Venon, Whitefish Bay, WI (US);
Gireesha Rao, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 2289 days.

(21) Appl. No.: 10/063,863

(22) Filed: May 20, 2002

(65) Prior Publication Data

US 2003/0216629 A1 Nov. 20, 2003

(51) Int. Cl.
*A61B 5/00* (2006.01)
(52) U.S. Cl. .................. 705/3; 705/2; 707/1; 324/309; 706/16; 706/20; 600/407
(58) Field of Classification Search .................. 600/407, 600/410, 425, 437, 438, 300; 382/128, 284; 378/162, 63; 705/2, 3, 7; 73/1.82; 707/1; 706/16, 20; 324/309
See application file for complete search history.

(56) References Cited

U.S. PATENT DOCUMENTS

| | | | | |
|---|---|---|---|---|
| 5,827,942 A | * | 10/1998 | Madsen et al. | 73/1.82 |
| 6,198,283 B1 | * | 3/2001 | Foo et al. | 324/309 |
| 6,394,353 B1 | * | 5/2002 | Schmitt | 378/162 |
| 6,418,334 B1 | * | 7/2002 | Unger et al. | 600/407 |
| 6,577,753 B2 | * | 6/2003 | Ogawa | 382/132 |
| 6,804,656 B1 | * | 10/2004 | Rosenfeld et al. | 705/3 |
| 2002/0057849 A1 | * | 5/2002 | Senda | 382/284 |
| 2002/0173721 A1 | * | 11/2002 | Grunwald et al. | 600/437 |
| 2003/0135389 A1 | * | 7/2003 | Gudapakkam et al. | 705/2 |
| 2003/0191509 A1 | * | 10/2003 | Flynn et al. | 607/60 |

\* cited by examiner

*Primary Examiner*—Brian Casler
*Assistant Examiner*—Baisakhi Roy
(74) *Attorney, Agent, or Firm*—Fletcher Yoder P.C.

(57) ABSTRACT

The present technique provides a system and method for dynamic configuration of medical diagnostic systems using distributable multi-component configuration files having extractable component-specific configuration data. The component-specific configuration data is extractable and processable at each component receiving a broadcast of the distributable multi-component configuration file. If a configuration change is desired in the system or in a particular component, then the change is made via the distributable multi-component configuration file. For example, the foregoing distribution and extraction techniques may be performed during operation of the distributed medical diagnostic system in response to a global or application change, such as different medical diagnostic applications. Accordingly, the present technique provides a flexible and architecture-independent mechanism for configuring components of a distributed medical diagnostic system.

20 Claims, 4 Drawing Sheets

TEXT-BASED GENERIC SCRIPT PROCESSING FOR DYNAMIC CONFIGURATION OF DISTRIBUTED SYSTEMS

BACKGROUND OF INVENTION

The present technique relates generally to medical diagnostic systems, such as medical imaging systems. In particular, the present technique provides a system and method for dynamic configuration of distributed medical diagnostic systems.

Existing medical diagnostic systems, such as medical imaging systems, use complex distributed architecture with multiple subsystems residing at different locations and on separate hardware platforms and separate operating systems. The configuration of subsystems within this distributed architecture is a complex procedure in which one or more of the subsystem components must have a configuration database with detailed information on all system components, which must be communicated to the appropriate subsystem component at a specific time. The foregoing configuration procedure causes performance bottlenecks, creates errors due to mismatches of duplicated application data on multiple subsystems, and precludes modification of the various system components.

For example, the existing system configures a medical diagnostic system for a desired application by exchanging system properties and data between multiple subsystems using application-specific information residing on one of the subsystems. Unfortunately, the foregoing configuration procedure increases the application setup time, because the application-specific information is not readily available at each component. Moreover, the existing configuration system is not scalable, because all of the involved components must be designed specifically for each application or the components must be configured for a specific application using configuration files and data from other components. The rigid characteristics of the existing configuration system generally preclude modification of the system configuration, particularly during runtime. The foregoing system is also ill suited for systems employing several different applications, such as Record Fixed and Record AEC applications of Digital Subtraction Angiography.

Accordingly, a technique is needed to facilitate dynamic configuration of multi-component systems, such as embedded or distributed medical systems. A need also exists for a flexible configuration system, which facilitates system modifications and execution at runtime.

SUMMARY OF INVENTION

The present technique provides a system and method for dynamic configuration of medical diagnostic systems using distributable multi-component configuration files having extractable component-specific configuration data. The component-specific configuration data is extractable and processable at each component receiving a broadcast of the distributable multi-component configuration file. If a configuration change is desired in the system or in a particular component, then the change is made via the distributable multi-component configuration file. For example, the foregoing distribution and extraction techniques may be performed during operation of the distributed medical diagnostic system in response to a global or application change, such as a change in medical diagnostic applications. Accordingly, the present technique provides a flexible and architecture-independent mechanism for configuring components of a distributed medical diagnostic system.

In one aspect, the present technique provides a medical diagnostic system comprising a plurality of medical diagnostic components communicatively coupled via communications circuitry. The system also comprises a dynamic configuration system for the plurality of medical diagnostic components. The dynamic configuration system has a configuration data distributor for multi-component configuration data, a component-specific data extractor for the multi-component configuration data, and a configuration data processor.

In another aspect, the present technique provides a medical diagnostic component comprising a configuration data provider of multi-component configuration data having extractable component-specific configuration data for a plurality of distributed medical diagnostic components. The medical diagnostic component also has a configuration data broadcaster of the multi-component configuration data to the plurality of distributed medical diagnostic components.

In another aspect, the present technique provides a medical diagnostic component comprising a configuration data receiver for a distributable multi-component configuration file, which comprises extractable component-specific application data for a plurality of medical diagnostic components. The medical diagnostic component also has a configuration data extractor and a configuration data processor of the extractable component-specific application data.

In another aspect, the present technique provides a configuration system for a medical diagnostic system. The configuration system comprises distribution means for distributing multi-component behavioral data to a plurality of medical diagnostic components. The configuration system also has processing means for processing component-specific portions of the multi-component behavioral data at each of the plurality of medical diagnostic components.

In another aspect, the present technique provides a method of configuring distributed components of a medical diagnostic system. The method comprises the act of distributing multi-component configuration data having extractable component-specific configuration data for a plurality of medical diagnostic components. The method also comprises the act of extracting the extractable component-specific configuration data from the distributed multi-component configuration data at each component of the plurality of medical diagnostic components. The method also comprises the act of processing the extractable component-specific configuration data extracted at each component.

In another aspect, the present technique provides a computer program for a medical diagnostic system. The computer program comprises a tangible medium configured to support machine-readable code and machine-readable code supported on the medium. The machine readable code comprises a broadcasting-component configuration system adapted to provide a multi-component configuration file having extractable component-specific configuration data for a plurality of medical diagnostic components.

BRIEF DESCRIPTION OF DRAWINGS

The foregoing and other advantages and features of the invention will become apparent upon reading the following detailed description and upon reference to the drawings in which.

DETAILED DESCRIPTION

The present technique provides a system and method for dynamic configuration of multi-components systems using a multi-component configuration system, which broadcasts multi-component configuration data/code for component-specific extraction at each component receiving the data/code. The multi-component configuration data/code may comprise a variety of configuration parameters, scripts (e.g., text-based scripts), executable code, execution triggers, and other desired data/code to facilitate operation of the system in various single-stage and multistage applications or procedures. For example, the present technique may distribute text-based scripts having a plurality of extractable component-specific information to configure, calibrate, diagnose, service, manage, or generally alter the behavior of the various components of a multi-component system, such as an embedded system or a distributed network system. Moreover, the present technique allows component operational characteristics to be added to existing behavioral characteristics for one or more components via the extractable component-specific information disposed within the multi-component configuration information.

In one exemplary embodiment, the present technique may broadcast multi-component configuration data/code for a particular medical diagnostic procedure to set up the various components for that specific procedure. Each component then extracts its component-specific portion of the multi-component configuration data/code and configures itself for that desired medical diagnostic procedure. Accordingly, the distribution and extraction process ensures that the various components operate in the desired manner for the particular application, architecture, or procedure. If the desired procedure has multiple stages, then the broadcast data/code may comprise multi-component configuration data/code for the multiple stages. Alternatively, the multi-component configuration data/code for subsequent stages may be distributed to the various components upon receiving a trigger or upon completion of the previous medical diagnostic stage. As discussed in further detail below, this multi-component configuration data/code distribution and extraction system facilitates dynamic configuration of the medical diagnostic system during runtime. The present technique also facilitates dynamic configuration based on a specific event, an interrupt, user input, or any other desired trigger.

Figure 1:
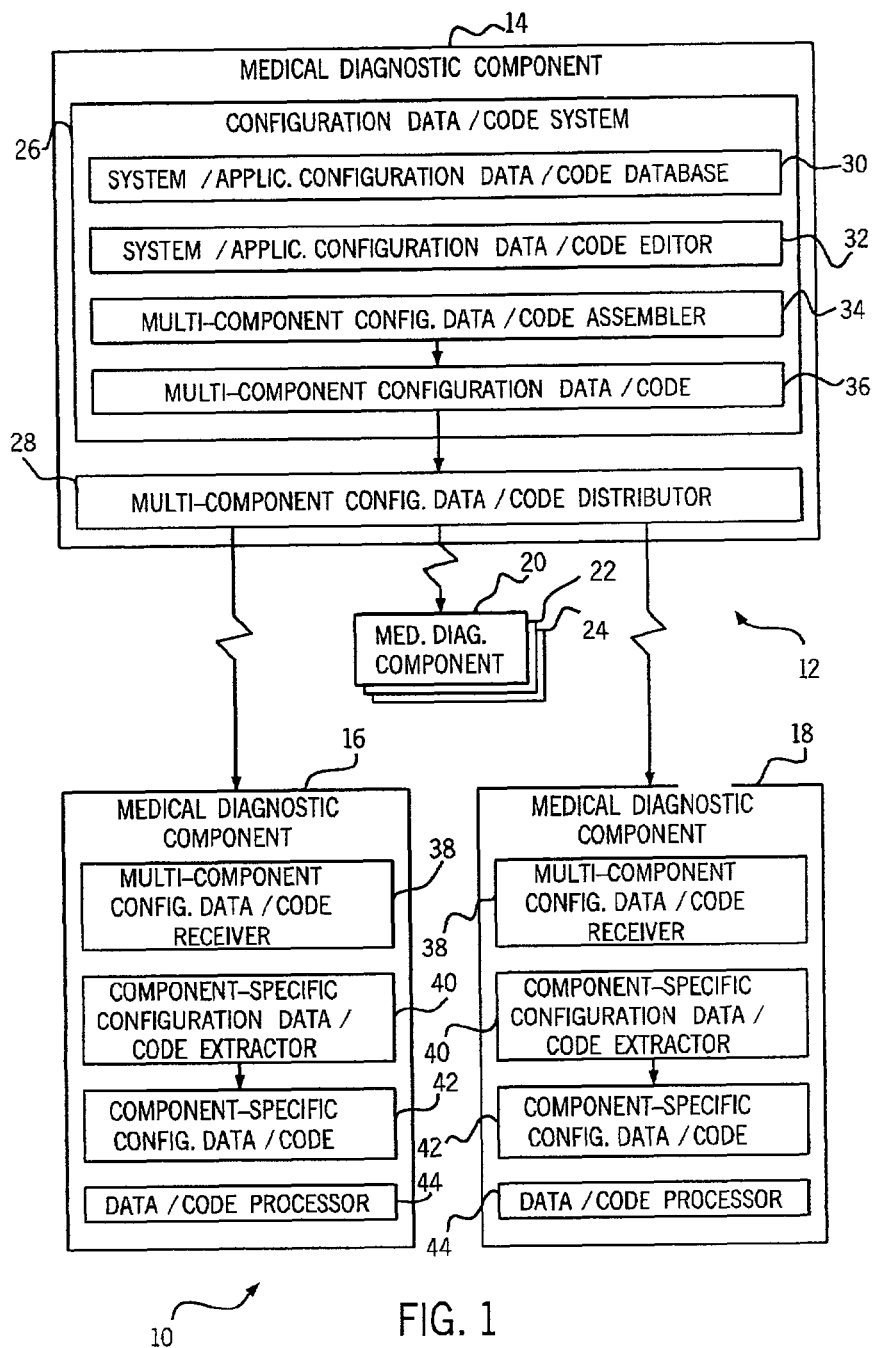
FIG. 1 is a diagram illustrating an exemplary multi-component configuration data/code distribution and extraction system disposed in a medical diagnostic system.

FIG. 1 is a diagram illustrating an exemplary multi-component configuration data/code distribution and extraction system 10 disposed in a medical diagnostic system 12, which comprises a plurality of medical diagnostic components or subsystems. In this exemplary embodiment, the medical diagnostic system 12 comprises medical diagnostic components 14, 16, 18, 20, 22, and 24. The medical diagnostic components 14-24 may comprise a variety of computer hardware and software, diagnostic acquisition components, diagnostic processing components, diagnostic-monitoring components, and user input components. For example, one or more of the medical diagnostic components 14-24 may have computing circuitry, a CPU, physical memory, communications circuitry, and editable component configuration parameters and operational characteristics. Moreover, the medical diagnostic components 14-24 may comprise medical components and subsystems in a variety of medical modalities and physical locations, such as different medical departments or facilities.

In the illustrated system 10 of FIG. 1, the medical diagnostic component 14 comprises a configuration data/code system 26 and a multi-component configuration data/code distributor 28. The illustrated configuration data/code system 26 comprises a system/application configuration data/code database 30, a system/application configuration data/code editor 32, and a multi-component configuration data/code assembler 34. The configuration data/code database 30 may comprise a variety of standard and customized text based scripts, code, information, system and component characteristics, specifications, application-specific behavioral parameters, stage/mode-specific behavioral parameters, and any other desired interpretable information, which may be used to configure, control, modify, or otherwise manage the various components of the medical diagnostic system 12. The foregoing information in the configuration data/code database 30 also may originate or result from user interaction with the configuration data/code editor 32, which may comprise a generic user interface, a generic code editor, a text-based editor, or any other suitable editor.

The multi-component configuration data/code assembler 34 provides multi-component configuration data/code 36, which is distributed to the various components of the medical diagnostic system 12 via the multi-component configuration data/code distributor 28. For example, the assembler 34 may gather and organize all or part of the information in the configuration data/code database 30 for a desired to medical diagnostic application, stage, or system procedure. Moreover, the assembler 34 may provide a user interface for user interaction during the assembly process, or the assembly 34 may interact with the editor 32 to allow modification for the particular procedure. In this exemplary embodiment, the assembly 34 may organize the medical diagnostic system/component information using component-specific tags, application-specific tags, stage/mode tags, medical modality tags, architectural tags, operating system tags, event triggers, or any other suitable parameters to facilitate the interpretation and extraction of the information by the components receiving the information. For example, the multi-component configuration data/code 36 may comprise a script or text file (e.g., a TCL script) having application-specific information for the various components of the medical diagnostic system 12. During an application set up stage or at any desired stage of the medical diagnostic system 12, the multi-component configuration data/code distributor 28 broadcasts the foregoing application-specific script or text file to the various components. The receiving components then extract component-specific information from the broadcasted file, as described below.

Each of the medical diagnostic components 16-24 comprises a multi-component configuration data/code receiver 38, a component-specific configuration data/code extractor 40, and a data/code processor 42. The receiver 38 may comprise communications circuitry and software, an initial information processor/analyzer, an information router, or any other information handling components. The extractor 40 may comprise any suitable organizational interpreter or processor, which evaluates the organization of the assembled multi-component configuration data/code 36, identifies the relevant component-specific portion of the data/code 36, and extracts that component-specific information for use on the component. Accordingly, the medical diagnostic components 16-24 receive the multi-component configuration data/code 36 from the distributor 28 via the extractor 38 and extract component-specific configuration data/code 44 via the extractor 40.

At the appropriate time (e.g., either immediate or upon receipt of a trigger), the data/code processor 42 then interprets and/or executes the component-specific configuration data/code 44 to set up the particular component for the desired application or stage. It should be noted that the data/code processor 42 may be acquired from another component upon initiation of the system 12 or at another desired time, such as along with the distribution of multi-component configuration data/code 36. If not immediately processed/executed at the component, then the component-specific configuration data/code 44 may be partially or entirely stored for subsequent processing upon receiving a trigger, upon changing stages of the medical diagnostic system 12, upon receiving user input, or upon occurrence of any other desired event. For example, the processor 42 may divide or organize the component-specific configuration data/code into subsections, such as different applications or modes of a multi-stage process. Each of these subsections may then be executed immediately, or a particular triggering event may be associated with the respective subsections. Upon receipt of the triggering event, the processor 42 then processes or executes the appropriate section of the component-specific configuration data/code 44.

Accordingly, the present technique facilitates automatic component configuration at each component using the distributed data/code, rather than requiring component-by-component manual configuration. The present technique also reduces configuration communications to a single broadcast, rather than requiring multiple and/or duplicate transmissions between the various components. The present distribution and extraction system 10 is also particularly advantageous for multistage or multi-application procedures, which may be efficiently configured and executed by passing triggers to the various components at the desired time for changing the stage or application of the system 12 via the distributed to and extracted data/code.

Figure 2:
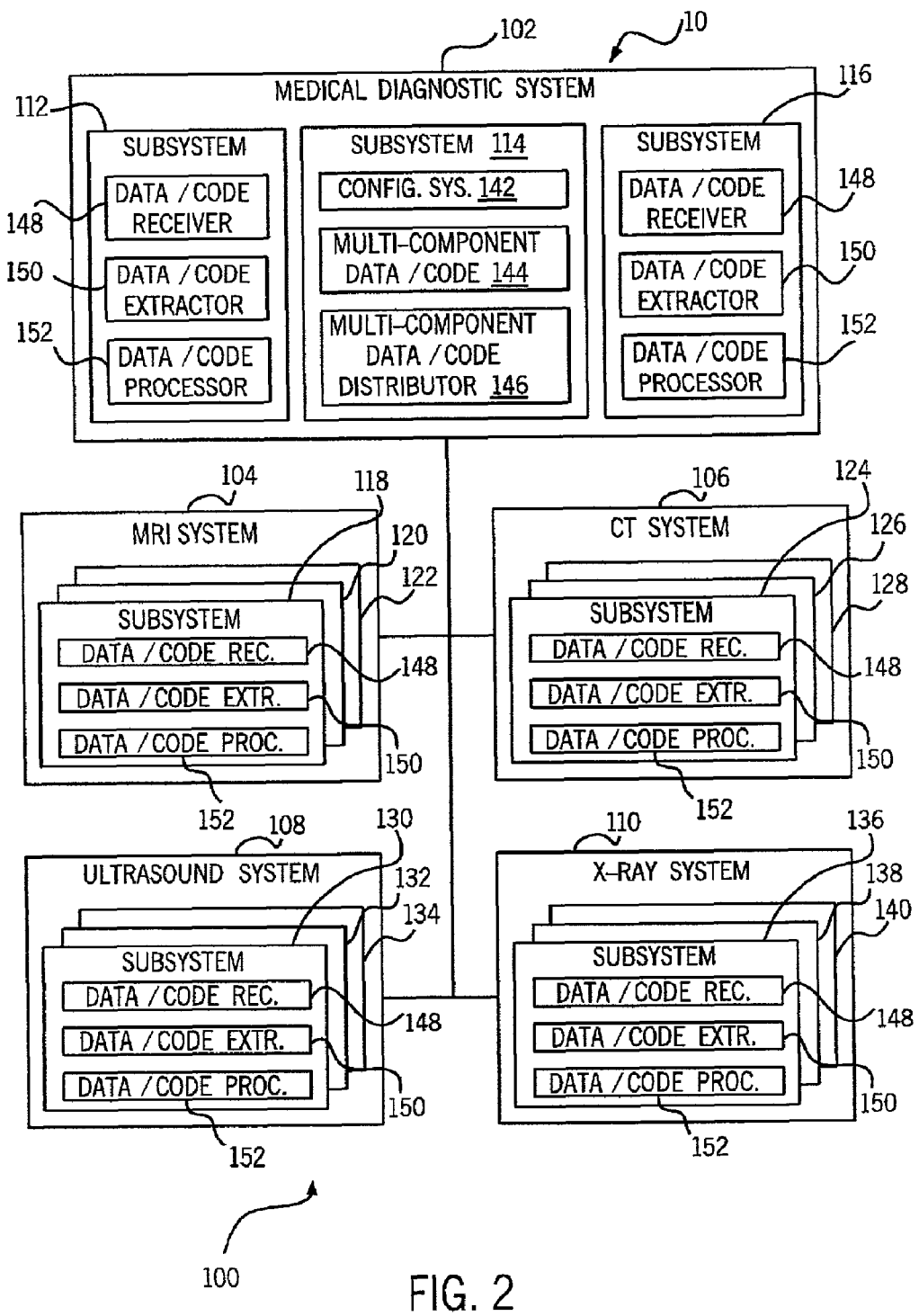
FIG. 2 is a diagram illustrating an exemplary medical diagnostic network having medical diagnostic systems of different modalities.

As mentioned above, the present technique is applicable to a variety of medical diagnostic systems and across multiple medical modalities. FIG. 2 is a diagram illustrating an exemplary medical diagnostic network 100 having medical diagnostic systems of different modalities. As illustrated, the medical diagnostic network 100 comprises a medical diagnostic system 102, a magnetic resonance imaging (MRI) system 104, a computed tomography (CT) system 106, an ultrasound system 108, and an x-ray system 110. However, the medical diagnostic network 100 may include any desired medical imaging or diagnostic system, including a variety of existing, ongoing, and future medical procedures. Each of the foregoing systems 102-110 may comprise one or more components or subsystems. For example, the systems 102, 104, 106, 108, and 110 comprise subsystems 112-116, 118-122, 124-128, 130-134, and 136-140, respectively.

In the medical diagnostic system 102 illustrated by FIG. 2, the subsystem 114 comprises a configuration system 142 to provide multi-component data/code 144, which may comprise a script or text file (e.g., a TCL script) having application-specific configuration information for various components of the medical diagnostic network 100. The subsystem 114 also has a multi-component data/code distributor 146, which broadcasts the multi-component data/code 144 to the desired components on the medical diagnostic network 100. Again, the data/code 144 may be transmitted upon initiation of a particular medical procedure, between stages of a multi-stage medical procedure, or upon receipt of any suitable triggering event, such as user input.

In this exemplary embodiment, each of the subsystems 118-140 comprises a data/code receiver 148, a data/code extractor 150, and a data/code processor 152. As described above with reference to FIG. 1, the receiver 148 may comprise communications circuitry and software, an initial information processor/analyzer, an information router, or any other information handling components. The extractor 150 may comprise any suitable organizational interpreter or processor, which evaluates the organization of the assembled multi-component data/code 144, identifies the relevant component-specific portion of the data/code, and extracts that component-specific information for use on the component. Accordingly, the subsystems 118-140 receive the multi-component data/code 144 from the distributor 146 via the receiver 148 and extract component-specific data/code via the extractor 150.

The data/code processor 152 then interprets and/or executes the extracted component-specific data/code to set up the particular component for the desired application or stage. Alternatively, the component-specific data/code may be partially or entirely stored for subsequent use upon receiving a trigger, upon changing stages of any one or all of the medical systems 102-110, upon receiving user input, or upon occurrence of any other desired event. The status of the particular component or subsystem also may trigger use of the component-specific data/code. For example, the data/code processor 152 may divide or organize the component-specific data/code into subsections, each of which may have a particular triggering event. Upon receipt of the triggering event, the data/code processor 152 then processes, executes, or otherwise interprets the appropriate section of the component-specific data/code.

Figure 3:
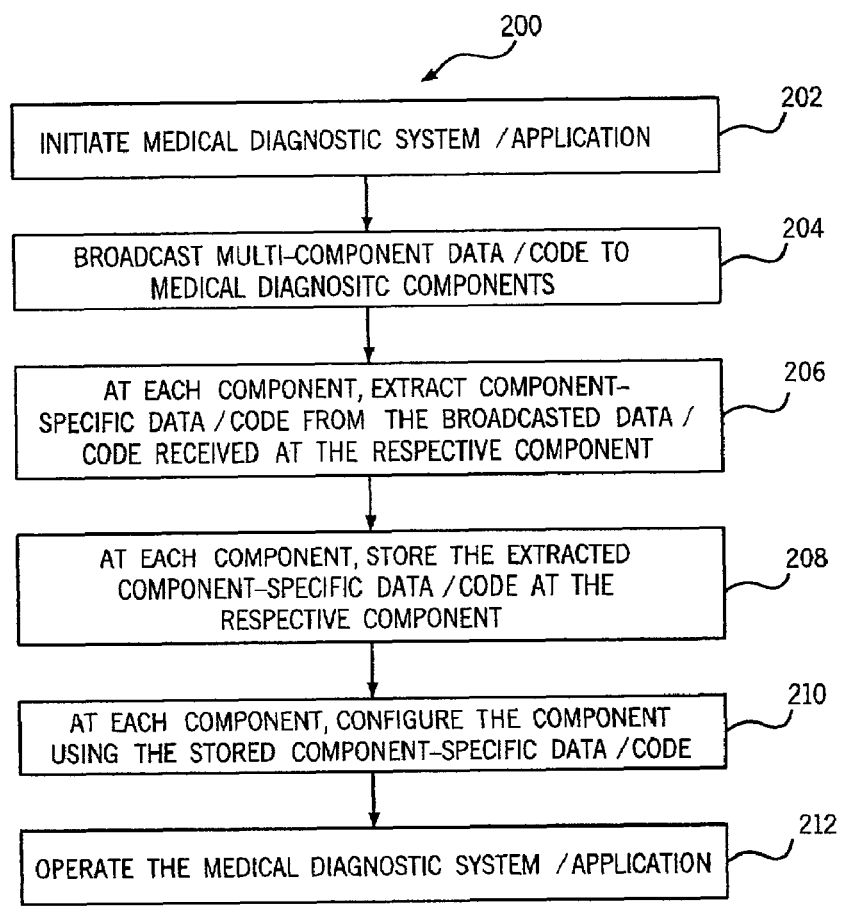
FIGS. 3 and 4 are flowcharts illustrating exemplary multi-component configuration and management processes of the present technique.
Figure 4:
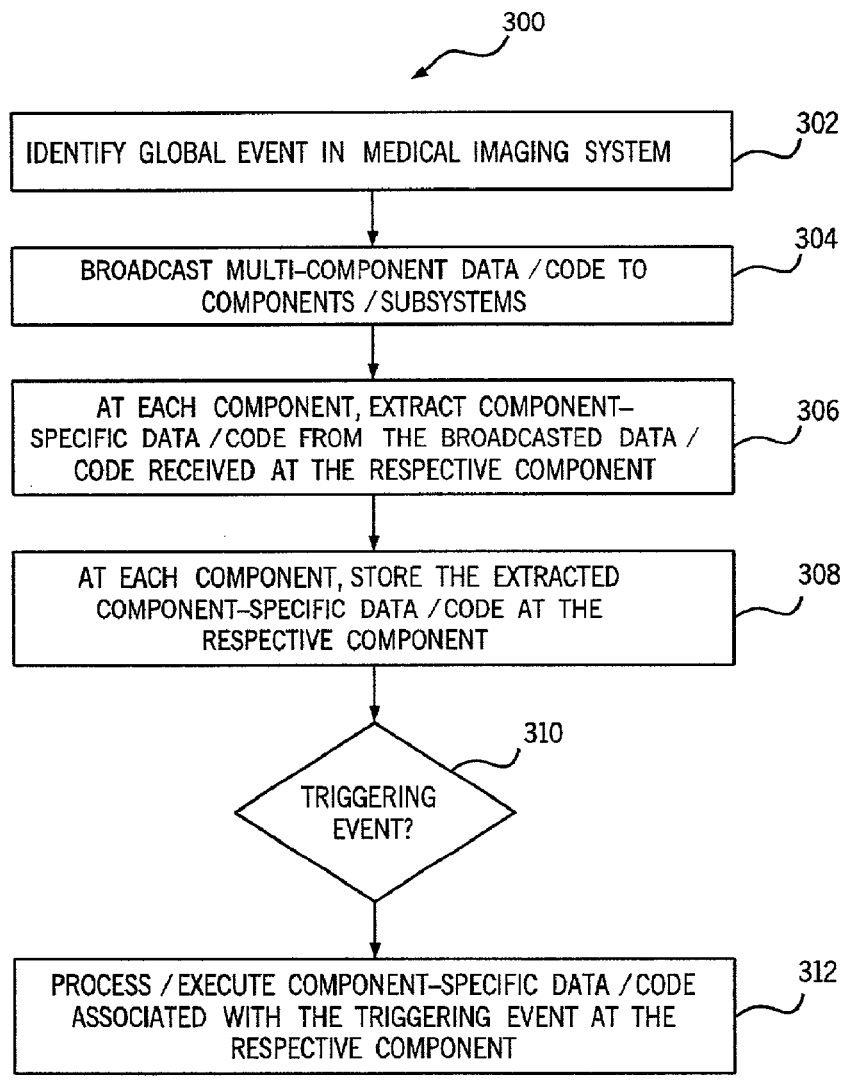

FIGS. 3 and 4 are flowcharts illustrating exemplary multi-component configuration and management processes 200 and 300 of the present technique. The multi-component configuration process 200 of FIG. 3 proceeds by initiating a medical diagnostic system/application, such as a medical imaging procedure (block 202). For example, the process 200 may initiate an imaging sequence or system, such as MRI, CT, Ultrasound, or X-Ray (e.g., Digital Subtraction Angiography). In some of these systems, the particular application may comprises multiple stages, such as the Record AEC and Record Fixed stages of Digital Subtraction Angiography. The process 200 also proceeds to distribute or broadcast multi-component data/code to the various medical diagnostic components (block 204). As discussed in detail above, the foregoing multi-component data/code may be assembled or provided via a database of component/system configuration information, user input, or any other suitable source. Each component within the distributed or embedded medical diagnostic system receives the broadcasted multi-component data/code. Upon receipt, each component extracts component-specific data/code from the broadcasted data/code (block 206). As noted above, this component-specific data/code may comprise process-specific information, application-specific information, modality-specific information, or any other organizable and extractable categories of information.

The process 200 also may store the data locally at the component if desired for subsequent processing, such as with multi-stage processing for multi-stage applications. Accordingly, the process 200 may proceed to store the extracted component-specific data/code locally at the respective component (block 208). The component-specific data/code extracted at each component is then used to configure each respective component (block 210). For example, each of the medical diagnostic components receives the multi-component configuration data/code, extracts its component-specific portion of the data/code, and processes/executes the data/code to self-configure the respective components. The process 200 then proceeds to operate the medical diagnostic system/application (block 212). This process 200 may be repeated entirely or partially at any time, such as during runtime of a multi-stage medical diagnostic procedure.

The multi-component management process 300 of FIG. 4 proceeds by identifying a global event in a medical imaging system (block 302). For example, the process 300 may identify a stage or application change in an imaging system, such as MRI, CT, Ultrasound, or X-Ray (Digital Subtraction Angiography). Upon identifying the global event, the process 300 proceeds to distribute or broadcast multi-component data/code to the various components/subsystems (block 304). As discussed in detail above, the foregoing multi-component data/code may be assembled or provided via a database of component/system configuration information, user input, or any other suitable source. Each desired component/subsystem within the distributed or embedded medical imaging system receives the broadcasted multi-component data/code. Upon receipt, each component/subsystem extracts component-specific data/code from the broadcasted data/code (block 306).

Again, the process 300 also may store the data locally at the component if desired for subsequent processing, such as with multi-stage processing for multi-stage applications. Accordingly, the process 300 may proceed to store the extracted component-specific data/code (block 308). The process 300 may then proceed to process/execute all or part of the component-specific data/code, or the process 300 may await a triggering event to process/execute all or part of the component-specific data/code (block 310). As noted above, if storage of the data/code is not desired at the various components, then the process 300 may simply proceed to process/execute the data/code at block 310. Moreover, the process 300 may divide the component-specific data/code into various subsections, each of which may have different triggering mechanisms. Upon receipt of the appropriate trigger, the process 300 proceeds to process/execute the appropriate component-specific data/code associated with the triggering event at the respective component (block 312). For example, the triggering event may execute an automatic configuration change of the particular component using all or part of the extracted component-specific data/code. If the extracted component-specific data/code comprises subsections for various applications or stages, then these various subsections may be processed/executed upon changing stages or applications.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A medical diagnostic system, comprising:
    a plurality of medical diagnostic components communicatively coupled via communications circuitry; and
    a dynamic configuration system for the plurality of medical diagnostic components, comprising:
        a configuration data distributor of multi-component configuration data to the plurality of medical diagnostic components, wherein the multi-component configuration data includes a file having application-specific information for at least two medical diagnostic components of the plurality of medical diagnostic components;
        a plurality of multi-component configuration data receivers, wherein each of the at least two medical diagnostic components of the plurality of medical diagnostic components includes a respective multi-component configuration data receiver of the plurality of multi-component configuration data receivers to allow each of the at least two medical diagnostic components to receive the file having application-specific information for all of the at least two medical diagnostic components;
        a plurality of component-specific data extractors of the multi-component configuration data, wherein each of the at least two medical diagnostic components of the plurality of medical diagnostic components includes a respective component-specific data extractor of the plurality of component-specific data extractors to enable each of the at least two medical diagnostic components to identify a relevant portion of the multi-component configuration data specific to the respective medical diagnostic component and to extract the relevant portion for use with the respective medical diagnostic component;
        a plurality of configuration data processors, wherein each of the at least two medical diagnostic components of the plurality of medical diagnostic components includes a respective configuration data processor of the plurality of configuration data processors to facilitate configuration of each of the at least two medical diagnostic components based on the relevant portion of the multi-component configuration data extracted by the component-specific data extractor of the respective medical diagnostic component.

2. The medical diagnostic system of claim 1, wherein the plurality of medical diagnostic components comprise imaging components.

3. The medical diagnostic system of claim 2, wherein the imaging components comprise magnetic resonance imaging components.

4. The medical diagnostic system of claim 2, wherein the imaging components comprise computed tomography components.

5. The medical diagnostic system of claim 2, wherein the imaging components comprise ultrasound components.

6. The medical diagnostic system of claim 2, wherein the imaging components comprise x-ray components.

7. The medical diagnostic system of claim 1, wherein the dynamic configuration system is operable at runtime of the medical diagnostic system.

8. The medical diagnostic system of claim 1, wherein the dynamic configuration system is architecture independent.

9. The medical diagnostic system of claim 1, wherein the dynamic configuration system is operable within a plurality of medical modalities for cross-modality deployment.

10. The medical diagnostic system of claim 1, wherein the configuration data distributor comprises an event-triggered broadcasting system.

11. The medical diagnostic system of claim 1, wherein the plurality of component-specific data extractors comprise a component-specific application separator.

12. The medical diagnostic system of claim 1, wherein the plurality of configuration data processors comprise a script interpreter for the multi-component configuration data.

13. The medical diagnostic system of claim 1, wherein the dynamic configuration system comprises a distribution triggering system.

14. The medical diagnostic system of claim 13, wherein the distribution triggering system comprises a user interface.

15. The medical diagnostic system of claim 13, wherein the distribution triggering system comprises an application event response system.

16. The medical diagnostic system of claim 13, wherein the distribution triggering system comprises a global mode monitoring system.

17. The medical diagnostic system of claim 13, wherein the distribution triggering system comprises a component status monitoring system.

18. The medical diagnostic system of claim 1, wherein the dynamic configuration system comprises a script generation system for the multi-component configuration data.

19. The medical diagnostic system of claim 1, wherein the configuration data distributor is disposed on at least one of the plurality of medical diagnostic components and the plurality of component-specific data extractors are disposed on remaining components of the plurality of medical diagnostic components.

20. The medical diagnostic system of claim 19, wherein the plurality of configuration data processors include a respective configuration data processor disposed on each of the remaining components.

* * * * *